(12) United States Patent
Kubon et al.

(10) Patent No.: US 10,483,708 B2
(45) Date of Patent: Nov. 19, 2019

(54) ENDOSCOPE HAVING A ROTATABLE ELECTRIC CONNECTING ELEMENT

(71) Applicant: Scholly Fiberoptic GmbH, Denzlingen (DE)

(72) Inventors: Massimo Kubon, Emmendingen (DE); Johannes Wickersheim, Malterdingen (DE); Jochen Dietrich, Elzach (DE); Patrick Spring, Freiburg (DE); Mateusz Cichosz, Freiburg (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 0 days.

(21) Appl. No.: 16/105,018

(22) Filed: Aug. 20, 2018

(65) Prior Publication Data

US 2019/0067891 A1 Feb. 28, 2019

(30) Foreign Application Priority Data

Aug. 28, 2017 (DE) ........................ 10 2017 119 691

(51) Int. Cl.
*H01R 35/02* (2006.01)
*H04N 5/225* (2006.01)
(Continued)

(52) U.S. Cl.
CPC ......... *H01R 35/025* (2013.01); *H04N 5/2252* (2013.01); *H04N 5/2253* (2013.01);
(Continued)

(58) Field of Classification Search
None
See application file for complete search history.

(56) References Cited

U.S. PATENT DOCUMENTS 3,599,165 A * 8/1971 Wendell ............... H01R 35/025
                                                              191/12 R
5,810,715 A * 9/1998 Moriyama ......... A61B 1/00078
                                                              600/139
(Continued)

FOREIGN PATENT DOCUMENTS

DE       19525686       1/1997
DE    102012206963     10/2012

OTHER PUBLICATIONS

"Flexible Electronics", In: Wikipedia, https://en.wikipedia.org/windex.php?title=Flexible_electronics&oldid=792481061.7/26/27 retrieved on Aug. 25, 2018, 3 pages.

*Primary Examiner* — Fernando Alcon
(74) *Attorney, Agent, or Firm* — Volpe and Koenig, P.C.

(57) ABSTRACT

A high-frequency transmission of data between functional units, which are mounted rotatably with respect to each other, of an endoscope, is permitted in which the functional units can be electrically insulated from each other. For this, an electric connecting element which, in a central flexible portion, is rolled up transversely with respect to the direction of transmission and is fastened by its respective end portions to the functional units is provided. An uninterrupted electrical connection with consistent quality of the signal transmission can therefore be obtained even when the functional units are rotated in relation to each other. By the rolling up of the central portion to form a winding, which is preferably configured in a self-supporting manner, a long term stable rotary degree of freedom is created in a very simple manner for the connecting element, with this degree of freedom permitting complex mechanical adjustment functions in the endoscope.

18 Claims, 3 Drawing Sheets

(51) Int. Cl.
  *H05K 1/02* (2006.01)
  *H05K 1/18* (2006.01)
  *H05K 5/06* (2006.01)

(52) U.S. Cl.
  CPC ........... *H05K 1/0278* (2013.01); *H05K 1/189* (2013.01); *H05K 5/06* (2013.01); *H04N 2005/2255* (2013.01); *H05K 2201/10121* (2013.01); *H05K 2201/10151* (2013.01)

(56) References Cited

U.S. PATENT DOCUMENTS

| | | | |
|---|---|---|---|
| 6,425,870 B1 | 7/2002 | Flesch | |
| 6,569,084 B1* | 5/2003 | Mizuno | A61B 1/00149 248/325 |
| 6,994,557 B2* | 2/2006 | Huscher | H01R 35/025 439/15 |
| 2005/0227521 A1* | 10/2005 | Dietrich | B60R 16/027 439/164 |
| 2009/0281387 A1* | 11/2009 | Takizawa | A61B 1/00082 600/117 |
| 2011/0201884 A1* | 8/2011 | Kishioka | A61B 1/00052 600/109 |
| 2014/0371534 A1* | 12/2014 | Okamoto | A61B 1/00066 600/118 |
| 2015/0079218 A1* | 3/2015 | Ohara | A61B 1/00165 425/383 |
| 2015/0208902 A1* | 7/2015 | Okamoto | G05G 5/05 74/501.6 |

* cited by examiner

ENDOSCOPE HAVING A ROTATABLE ELECTRIC CONNECTING ELEMENT

INCORPORATION BY REFERENCE

The following documents are incorporated herein by reference as if fully set forth: German Patent Application No. 10 2017 119 691.9, filed Aug. 28, 2017.

BACKGROUND

The invention relates to an endoscope having two functional units which are rotatable in relation to each other, and having an electric connecting element by which the two functional units are connected or are connectable electrically to each other.

In order to impart functions, such as a mechanical zoom or focus adjustment or a mechanical image horizon orientation, for example to video endoscopes, certain components of the endoscope have to be mounted rotatably. If said components also comprise or contact electronic connections or printed circuit boards, the respective electronic connections also have to be ensured between components or functional units which are rotatable in relation to one another. It is a challenge in this connection to provide an electric connecting element which permits an as resistance-free rotation as possible of functional units which are connected electrically to one another by the connection, and at the same time does not impair the electronic signal transmission between the functional units.

In order to transmit electric signals between endoscope components which are mounted rotatably with respect to one another, use is frequently made in the prior art of sliding contacts, in particular rotational sliding contacts, or flexible spring contacts. However, contacts of this type are subject to wear and are prone to malfunction. Furthermore, such contacts produce a high electrical impedance and capacitance at the contact points which also change during movement of the components. Such contacts are therefore suitable at most for low-frequency or frequency-independent electric signals. By contrast, contacts of this type are unsuitable for signals with frequencies in the MHz to GHz range, as are used in particular in order to permit a high data transmission rate. This is the case, for example, in video endoscopes or camera heads.

SUMMARY

The invention is therefore based on the object of producing an electronic connection between two functional units, which are rotatable in relation to each other, of an endoscope and, in the process, of ensuring as high a quality as possible of the signal transmission, even when high signal frequencies are used. Available technologies for electronic components are preferably intended to be used for this purpose. Further aims include simple production and a long service life of the connection.

In order to achieve this object in the case of an endoscope, one or more features of the invention are provided. In particular, according to the invention, in order to achieve the object it is therefore provided, in the case of an endoscope of the type mentioned at the beginning, that the electric connecting element, at least in a flexible portion, is placed into a winding.

By use of the winding, it is first of all possible to allow the connecting element a rotary degree of freedom. Rotation of the functional units in relation to each other is therefore permitted, while maintaining an electric connection. In addition, unlike in the case of conventional sliding contacts, no additional impedances or capacitances occur in the signal chain. In the case of the connecting element according to the invention, even a relative movement of the functional units in relation to each other does not have a negative effect on the quality of the signal transmission.

With the invention, in particular live image data of a video endoscope can therefore be transmitted without disturbance, specifically with the use of data transmission rates as are otherwise possible only with conventional rigid printed circuit boards, which specifically do not have any rotary degrees of freedom.

The object can also be achieved by further advantageous developments of the invention as described below.

The connecting element can thus be held, in particular exclusively, by the two functional units. The flexible portion which forms the winding can therefore be arranged in particular in a self-supporting manner. By the self-supporting design of the winding, an additional (rotational) mounting of the connecting element can be dispensed with. For example, the formation of ball bearings within a housing of the endoscope for mounting the electronic connection may no longer be required as a result.

It is therefore possible inter alia to form the endoscope housing hermetically and to insulate same electrically from the connection, which is required in many medical applications of endoscopes. For example, a high-frequency video signal, a supply of voltage, control signals and electrical shielding can be transmitted by a connecting element according to the invention.

In a preferred refinement of the invention, the winding is designed in the form of a band. As a result, a controlled deformation of the winding is possible during rotation of the two functional units in relation to each other without individual turns of the winding interlocking with one another.

Within the context of the invention, it is furthermore of great advantage if the winding itself is dimensionally stable. This is because, in this case, a winding shape once produced by winding can be maintained permanently, which permits a reproducible winding up and unwinding.

According to another advantageous refinement, a particularly reliable, reproducible and space-saving deformation of the winding can be achieved if the winding is formed in a spiral manner, preferably in the form of a flat spiral. If the spiral has a plurality of turns, the connecting element can have a rotary adjustment range of +/−180° or more. In the case of a high number of turns, more than +/−360° can even be realized. Depending on the available construction space, a very wide variety of spiral shapes can be used here according to the invention; for example, Archimedes', logarithmic or Fermat's spiral shapes can be used. With the latter spiral shape, it is possible, for example, to in each case arrange rigid portions of the connecting element, which portions are not wound, in a decentralized manner with respect to the center of the spiral.

By contrast to conventional sliding contacts, such refinements of the connecting element according to the invention afford the advantage that the electronic connection can be configured virtually free from material fatigue. This is because the arrangement of the flexible portion in the form of a spiral makes it possible to avoid plastic deformations, and therefore the rotary movability can be obtained solely on account of elastic deformation.

According to an advantageous refinement, a particularly compact constructional form can be obtained by the fact that the two functional units are rotatable with respect to each other about a common axis of rotation which coincides with a central winding axis of the winding.

A further refinement proposes that the flexible portion is elastically deformable, preferably transversely with respect to the previously described axis of rotation. It is therefore possible in particular to produce a prestress by the winding. Furthermore, the elastic deformability ensures that the winding is guided permanently and remains positioned in a defined manner. Furthermore, material fatigue, as occurs in the case of plastic deformations, can be avoided.

Due to the elastic and in particular reversible deformability of the flexible portion, a resetting force is also produced which the electric connecting element exerts on the two functional units.

In certain embodiments, a manual actuating unit, for example in the form of a rotary handle, can be provided on the endoscope and with which the second functional unit is adjustable or rotatable in relation to the first functional unit. It can be advantageous here if the actuating unit is formed with its own friction which is greater than the resetting force introduced by the electric connecting element. It can thereby be avoided that the second functional unit is adjusted inadvertently relative to the first functional unit.

According to a particularly advantageous refinement, the winding is designed in the form of a, preferably band-shaped, spiral spring. This spiral spring can be designed in particular in such a manner that, when the two functional units rotate in relation to each other, the spiral spring permits a reversible elastic deformation of the connecting element out of an inoperative position. The spiral spring can generate a resetting force during deformation out of the inoperative position. In the inoperative position, which can be used as the central position, the winding and therefore the spiral spring by contrast specifically exert only a very small resetting force if any at all.

In order to permit as stable positioning as possible and a simple installation of the connecting element, it is provided in a further refinement that the connecting element has a first rigid portion and a second rigid portion. The flexible portion can therefore be in particular a central flexible portion. The flexible portion can therefore connect the two rigid portions to each other. It is preferred here if said connection is formed in a manner free from connecting plugs.

In a further preferred refinement, the first and/or the second rigid portion protrudes/protrude over the central flexible portion in the direction of the axis of rotation, preferably at least by a width of the central flexible portion. It is preferred in this connection if the two rigid regions overlap only in the region of the central flexible portion. By these refinements, firstly stable transitions are in each case provided between the flexible and the rigid regions, starting from which transitions a flat spiral winding can be wound up and unwound in a reproducible manner. Secondly, electronic components can be arranged on the rigid regions of the connecting element that protrude over the winding, in order to permit complex signal transmissions and control and regulating loops.

In order to permit a winding here which is as resistance-free and space-saving and as flat as possible, it is furthermore of advantage if the central flexible portion in each case contacts the two rigid portions in the direction of the winding, i.e. in particular transversely with respect to the axis of rotation. The winding direction is oriented here transversely with respect to the axis of rotation.

By the use of industrially tried and tested flexible printed circuit board technology, the connecting element can be produced in a particularly simple and cost-effective manner. The connecting element can therefore be manufactured integrally, preferably from a multi-layered printed circuit board. The flexible portion can advantageously be formed here by a material weakening or by simple omission of material, in particular of individual layers of the printed circuit board.

A further improvement can be achieved if a wedge is formed at at least one transition between a rigid portion and the central flexible portion, said wedge conducting away bending forces which occur to the transition. When a printed circuit board is used, such a wedge can be formed in a simple manner from adhesive. By conducting away the bending forces, stress concentrations are avoided at the transitions between the flexible and the rigid portions. Service lives of, for example, more than 40,000 load changes with rotations about +/−100° on the winding can therefore be obtained.

If conventional printed circuit boards are used for producing the connecting element, it is advantageous for sufficient flexibility if the number of layers of the printed circuit board in the central flexible section is at least two less than the number of layers in the two rigid portions.

Furthermore, in order to achieve a uniform electrical impedance of the connecting element, a metallized layer of the printed circuit board that is used for shielding can be formed in the region of the central flexible portion not, as customary, in the form of full metallization, but rather in the form of a perforated grid.

In the rigid regions, the printed circuit board can have reinforcements, for example by layers of FR-4 material. However, even in the case of such a design, it is possible for the strip conductors of the printed circuit board to run without obstruction, i.e. in particular in an unchanged and/or transition-free manner, from the rigid region into the flexible region.

With regard to the configuration of strip conductors on the printed circuit board, strip conductors which are pressed onto individual layers of the printed circuit board are preferred according to the invention. This is because, unlike strip conductors which are galvanized on, these strip conductors age less rapidly during elastic deformations of the flexible portion of the printed circuit board.

According to a specific refinement of the endoscope, it can be provided that the first rigid portion of the connecting element is connected non-rotatably to a housing of the endoscope. The second rigid portion can be connected here non-rotatably to an inner coupling element which is arranged in the interior of the housing. As previously described, the endoscope can have an outer actuating element which serves as a coupling element and with which torques can be transmitted to the inner coupling element from the outside. A refinement is therefore described in which an inner coupling element which is actuatable from the outside is electrically connected by a connecting element according to the invention to an endoscope housing, which is arranged rotatably relative to the inner coupling element.

According to a further refinement, it is advantageous if the winding forms at least two complete turns. This is because a greater number of turns causes the resetting force of the connecting element to be more homogeneous over the rotary adjustment range. In addition, the spring constant of the spiral spring can be set by the number of turns. The spring constant has an effect, inter alia, on the service life of the connecting element. However, too high a number of turns should be avoided for space-saving reasons since, for a predetermined angle of rotation, the change in the diameter of the winding becomes greater the more turns the winding has.

The winding can be configured in a particularly compact manner in particular if the winding (and the spiral spring which therefore arises and has already been described previously) is designed in the form of an Archimedes spiral. The spiral can therefore be configured in particular in such a manner that a radius of the spiral spring increases linearly or at least monotonously as the angle increases. In the case of a linear increase, it is of advantage here for the turns to be able to be arranged equidistantly with respect to one another, which permits a compact constructional form.

It can therefore be provided in particular that turns of the winding, i.e. in particular the previously described more than two turns, are spaced apart from one another in an inoperative position. In this connection, the winding and therefore the connecting element specifically do not exert any resetting force in the inoperative position. It is of advantage in the case of this refinement that the winding can be rotated from the inoperative position as the central position in both directions. A large rotary adjustment range is therefore possible. This applies in particular in the case of the design of the winding in the form of a spiral.

The previously described windings and spiral springs can be manufactured particularly simply if the winding is wound from a flat blank. Conventional, two-dimensional, flat printed circuit boards can therefore be used for manufacturing the connecting element.

If the endoscope has a hermetic housing, the electric connecting element can also be electrically insulated from the housing and arranged in the interior of the housing. For this purpose, in particular a rigid portion of the connecting element can be held by an electric leadthrough, in particular by plug-in contacts. Such an electric leadthrough can be configured, for example, as a glass leadthrough on the housing of the endoscope. If the leadthrough is arranged here centrally with respect to a cross section of the housing, a particularly compact constructional form can be obtained. With the invention, it is therefore possible in particular to provide what is referred to as a "virtual ground" in the endoscope, in particular in the endoscope tip, which virtual ground is electrically separated from a shielding of the housing.

According to the invention, it is of advantage if the connecting element is held only in each case in the region of the two rigid portions. This is because the central flexible portion can therefore be formed in a free-standing manner. This avoids friction and permits a simple installation. In addition, a self-supporting configuration of the winding is of great advantage for a miniaturized constructional form, as is necessary in endoscopes, since, unlike in the case of known macroscopic cable drums or the like, no further parts have to be fitted.

A particularly compact and miniaturized arrangement of the winding can be obtained if the first or the second rigid portion is arranged in a center of rotation of the winding, i.e. in particular in a center of rotation of the spiral spring. In this case, in particular this rigid portion which is arranged in the center of the winding can be arranged in a free-standing manner in the region of the winding.

In order to permit miniaturization and simple installation of a connecting element according to the invention, it is advantageous if the winding can be wound up and unwound automatically without assisting means, by rotation of the two functional units in relation to each other. For this purpose, a further configuration proposes that intermediate spaces are kept free between individual turns of the winding, preferably along the entire length of the winding.

The winding can therefore be arranged in particular without a carrier, i.e. in particular in a core-free and/or self-supporting manner. It is preferred here if the winding is kept in a spiral shape in the radial direction free from contact with other bodies and only on account of its own dimensional stability. For this purpose, a receiving space can be formed in the endoscope, said receiving space receiving the winding in a contact-free manner in the radial direction both during the winding up and during the unwinding. In order to permit as resistance-free rotation as possible of the connecting element, the winding can therefore be configured in such a manner that the winding is held in a freely movable and/or contact-free manner in the radial direction, preferably over an entire rotary adjustment range of the spiral spring.

In order, by contrast, to avoid an uncontrolled winding up or tilting of the winding in the axial direction, a further preferred refinement finally provides that either the first and/or the second functional unit provides at least one axial stop surface which axially limits the movement of the winding, during the rotation of the functional units in relation to each other.

The invention is usable in particular in what are referred to as chip-in-tip endoscopes which typically have an image sensor which is arranged rotatably in relation to an endoscope housing. Consequently, the first functional unit of the endoscope can have, for example, an endoscope housing, an endoscope shaft and an imaging lens arranged therein. The first functional unit can furthermore have a shielding connection which connects a coaxial shielding of a connection cable to a housing of the endoscope.

By contrast, the second functional unit can be connected non-rotatably to an image sensor which is mounted downstream of the imaging lens. If the lens realizes an angling of the field of vision, the viewing field of the endoscope can be changed by rotation of said lens.

The rotatable mounting of the image sensor here ensures that the image sensor does not have to change its spatial position (and therefore the horizon position), and therefore the image horizon perceived by the user of the endoscope can be maintained even when the viewing field of the endoscope tip changes. For this purpose, the image sensor can be rotated in relation to the endoscope housing and therefore in relation to the lens, for example, by an outer rotary wheel which is formed on the endoscope housing.

In the case of such an endoscope, it is typically required for electric lines which are supplied via a cable to the endoscope housing from a camera control unit are electrically connected to the image sensor. It can be ensured here by the invention that signals can be reliably transmitted from the camera control unit to the rotatably arranged image sensor and also in the reverse direction. This applies even if high signal frequencies are used for the transmission. In order to be able to realize this functionality, a further advantageous refinement therefore provides that the second functional unit bears an image sensor and the first functional unit bears an object-side lens which is assigned to the image sensor.

In a refinement of the invention, it can be provided that the connecting element bears an electronic circuit in at least one end portion. An electric connection to an electronic circuit, for example to an adaptation circuit and/or to a signal processing circuit, can therefore already be produced before final installation and/or in a plug-free manner. This simplifies the final installation. This end portion is preferably the rigid portion which has already been mentioned, in particular in the case of an integral connecting element, for example manufactured from a printed circuit board. An electronic circuit is in each case preferably formed in each of the two end portions of the connecting element, in particular in each of the rigid portions which have already been described. This is because the overall area of the connecting element can thus be optimally utilized. In addition, the placing of an electronic circuit on an end portion of the connecting element has the advantage that the winding is not mechanically impaired by components, and that an electrical inductance which inevitably arises because of the winding can be compensated for by corresponding, electrically capacitive elements.

Further applications of the inventions relate to endoscopes in which a focus or zoom setting is made possible by outer rotary rings or the like. Functional units in the interior of the endoscope, for example an adjustable lens with illumination LEDs, which are rotated in relation to a housing of the endoscope as a further functional unit, can also be electrically contacted here by a connecting element according to the invention.

BRIEF DESCRIPTION OF THE DRAWINGS

The invention is now described in more detail with reference to exemplary embodiments, but is not restricted to these exemplary embodiments.

Further exemplary embodiments emerge by combining the features of individual claims or of a plurality of claims with one another and/or with individual features or a plurality of features of the respective exemplary embodiment. In particular, developments of the invention can therefore be obtained from the description below of a preferred exemplary embodiment in conjunction with the general description, the claims and the drawings.

In the drawings.

DETAILED DESCRIPTION

Figure 1:
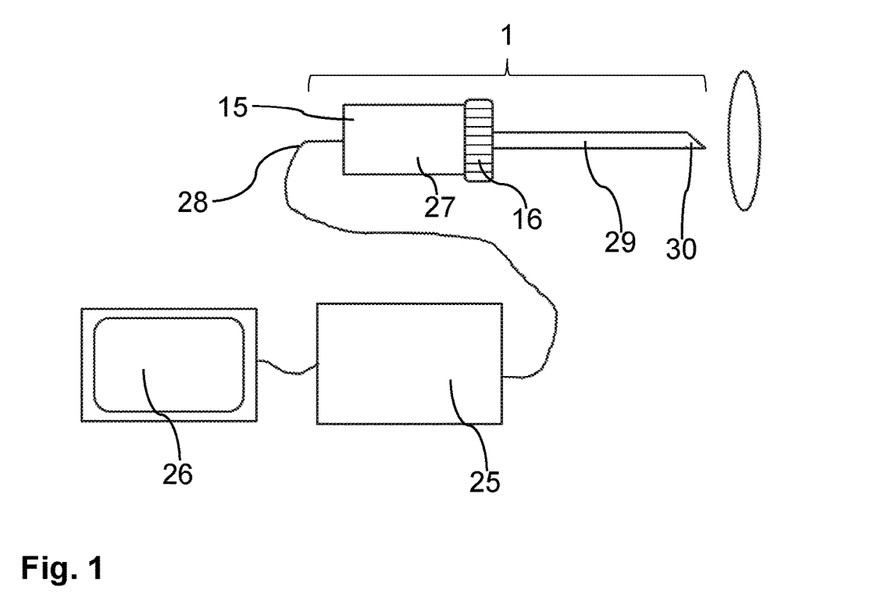
FIG. 1 shows a schematic overview illustration of an endoscope according to the invention with further connected units.
Figure 2:
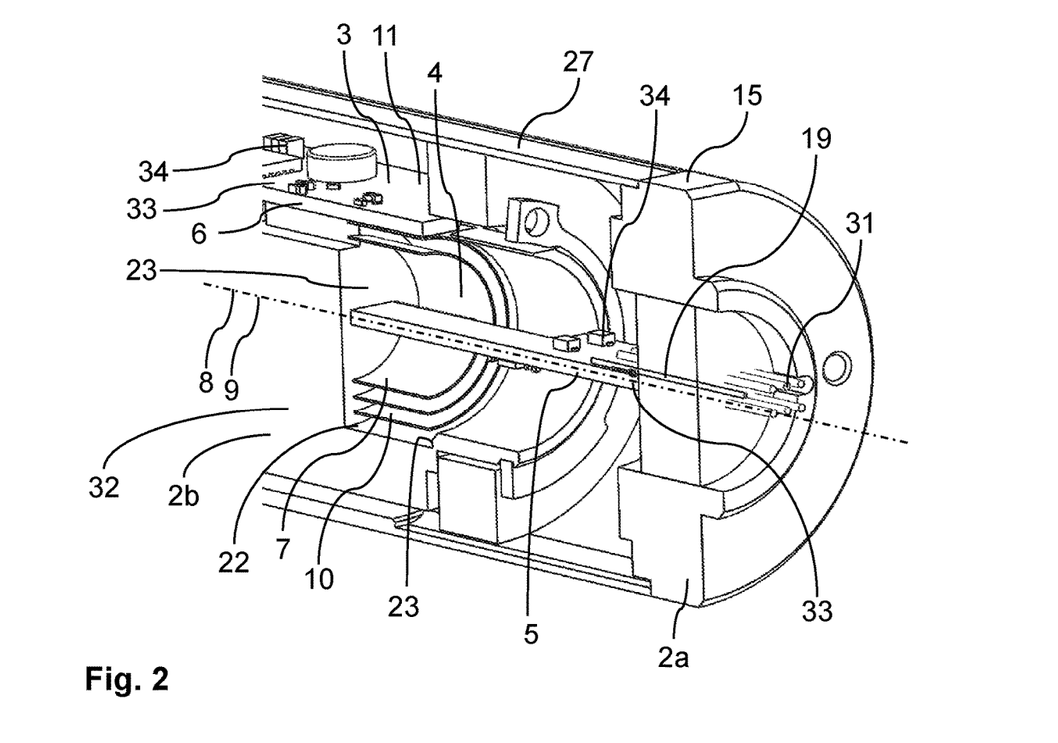
FIG. 2 shows a longitudinal section through an endoscope according to the invention in the region of the handle which discloses the arrangement of an electric connecting element according to the invention.

FIG. 1 shows an endoscope, which is denoted in its entirety by 1, with a handle 27, a rotary wheel 16 and with an endoscope shaft 29. An image sensor which is connected to the heat sink which is denoted by 32 in FIG. 2, is located in the endoscope tip 30. This heat sink 32 is mounted rotatably in relation to the endoscope housing 15. The image sensor can be rotated in relation to the housing 15 and the endoscope shaft 29, which is rigidly connected thereto, with the rotary wheel 16, which is coupled to the heat sink 32 in the interior of the endoscope 1. The rotary wheel 16 and the heat sink 32 therefore constitute an outer or inner coupling element.

In addition, an imaging lens is located in the endoscope tip 30 and, for its part, is connected non-rotatably to the endoscope shaft 29 and therefore to the housing 15. Video signals are transmitted by a camera cable 28 from the image sensor of the endoscope 1 to a camera control unit 25 which transmits the images to a monitor 26.

If the endoscope housing 15 and therefore the imaging lens are rotated, the viewing direction in the case of the endoscope 1 in FIG. 1 is changed. The image sensor can be secured here in its current spatial position by the rotary wheel 16 such that the image horizon is maintained for the observer.

As FIG. 2 shows, the handle 27 is connected non-rotatably to the housing 15 which forms a first functional unit 2a together with the imaging lens of the endoscope 1. A second functional unit 2b is formed by the heat sink 32 and the image sensor which is connected thermally and mechanically thereto and is arranged (and not illustrated in FIG. 2) in the endoscope tip 30. The second functional unit 2b is therefore arranged within the endoscope housing 15 and is mounted rotatably here in relation to the first functional unit 2a.

The image sensor of the endoscope 1 is electrically connected to a second rigid portion 6 of a printed circuit board 11, as can readily be seen in FIG. 2. The second rigid portion 6 is electrically connected here to a first rigid portion 5 by a flexible central portion 4 of the printed circuit board 11 (also see FIG. 3), which portion is wound up in the form of a spiral spring 10. While the second rigid portion 6 is connected non-rotatably to the heat sink 32, the first rigid portion 5 is held by an electric leadthrough 19, more precisely by plug-in contacts 31 of the electric leadthrough 19, which are electrically insulated from the housing 15. The leadthrough 19 is formed here in the endoscope housing 15 centrally with respect to a cross section of the endoscope housing 15 at the proximal end of the endoscope 1. The first rigid portion 5 is therefore connected non-rotatably to the housing 15 and therefore to the first functional unit 2a. The first rigid portion 5 therefore rotates together with the endoscope housing 15 and with the handle 27.

Due to the leadthrough 19, first of all the housing 15 is overall hermetically sealed and secondly the connecting element 3 is arranged in an electrically insulated manner from the housing 15. Therefore, with the aid of one of the plug-in contacts 31 in FIG. 2, a "virtual ground" can be guided into the interior of the endoscope 1 and from there with the aid of the connecting element 3 into the endoscope tip 30.

Figure 3:
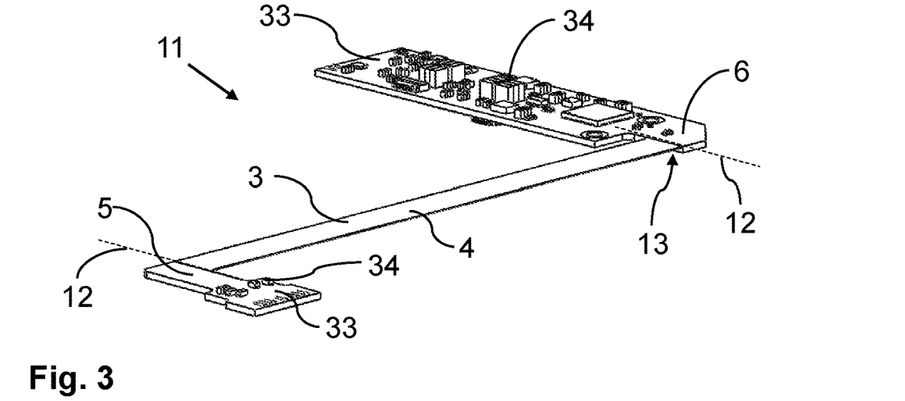
FIG. 3 shows a perspective view of an isolated printed circuit board from which an electric connecting element according to the invention can be produced by winding up.

As FIG. 3 shows, the printed circuit board 11 from FIG. 2 includes the two rigid portions 5 and 6 and the central flexible portion 4. The printed circuit board 11 therefore forms an electric connecting element 3 with which video signals can be transmitted from the image sensor to the plug-in contacts, which are denoted by 31 in FIG. 2. The plug-in contacts 31 serve for the connection of the camera cable 28 from FIG. 1.

Electronic circuits 34 are in each case arranged on the two end portions 33 of the printed circuit board 11, which end portions in the case of the exemplary embodiment shown in FIG. 3 are identical to the two rigid portions 5 and 6, while the central portion 4 is kept free from electronic components. The latter is advantageous in order firstly to ensure a uniform elasticity of the central portion 4 and secondly to permit as tight a winding as possible of the central portion 4. The electronic circuit 34 on the second rigid portion 6 serves here for activating and regulating the image sensor of the endoscope 1. As can be seen in FIG. 3, electronic components can be placed here both on upper sides and lower sides of the end portions 33.

Figure 4:
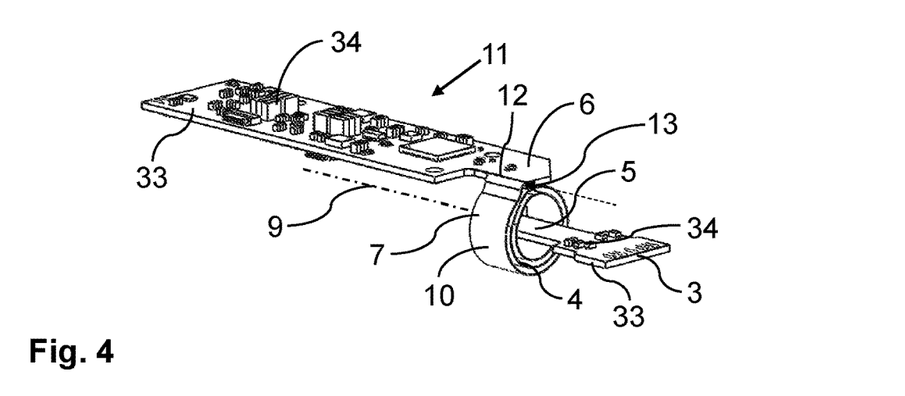
FIG. 4 shows the printed circuit board from FIG. 3, after the winding up of the central flexible portion to form a spiral spring.

It becomes apparent with reference to FIG. 3 that, by rolling up or winding up the central portion 4 of the printed circuit board 11 from FIG. 3 about the winding axis, denoted by 9 in FIG. 4, a spiral winding 7 is produced. This winding 7 imparts a rotary degree of freedom to the connecting element 3. In other words, the two functional units 2a and 2b and the rigid portions 5 and 6, which are fixedly connected thereto, of the printed circuit board 11 can be rotated in relation to each other about the axis of rotation, which is denoted by 8 in FIG. 2, without the electric connection between the image sensor and the plug-in contacts 31 being impaired in the process. For this purpose, it is favorable if the winding axis 9 of the connecting element 3 coincides precisely with the axis of rotation 8, as shown in FIG. 2.

As can also readily be seen in FIGS. 3 and 4, electronic components can be arranged on the connecting element 3 according to the invention, and therefore complex electronic functions can be undertaken by the connecting element 3. However, it is of great advantage in this case if the central flexible portion 4 merely has strip conductors and shieldings, but no electronic components. This is because a high degree of flexibility and elasticity of the central portion 4 can therefore be ensured as a prerequisite for easy rotatability.

As is apparent from the overall view of FIGS. 3 and 4, the winding 7 is wound from a flat blank and is spiral-shaped. On account of its band shape and the elasticity of the central flexible portion 4 of the printed circuit board 11 from FIG. 3, the winding 7 is also dimensionally stable. This permits the self-supporting arrangement, which can be seen in FIGS. 2, 4 and 6, of the spiral spring 10 formed by the winding 7.

Due to the elastic deformability of the central portion 4, the connecting element 3 overall can be reversibly and elastically deformed, wherein the two rigid portions 5 and 6 are specifically not deformed here. By suitable selection of the cross section of the central portion 4 and of the number of turns 17 of the winding 7, a resetting spring force can be set here which the spiral spring 10 exerts on the two functional units 2a and 2b on deflection out of its inoperative position 18.

Figure 6:
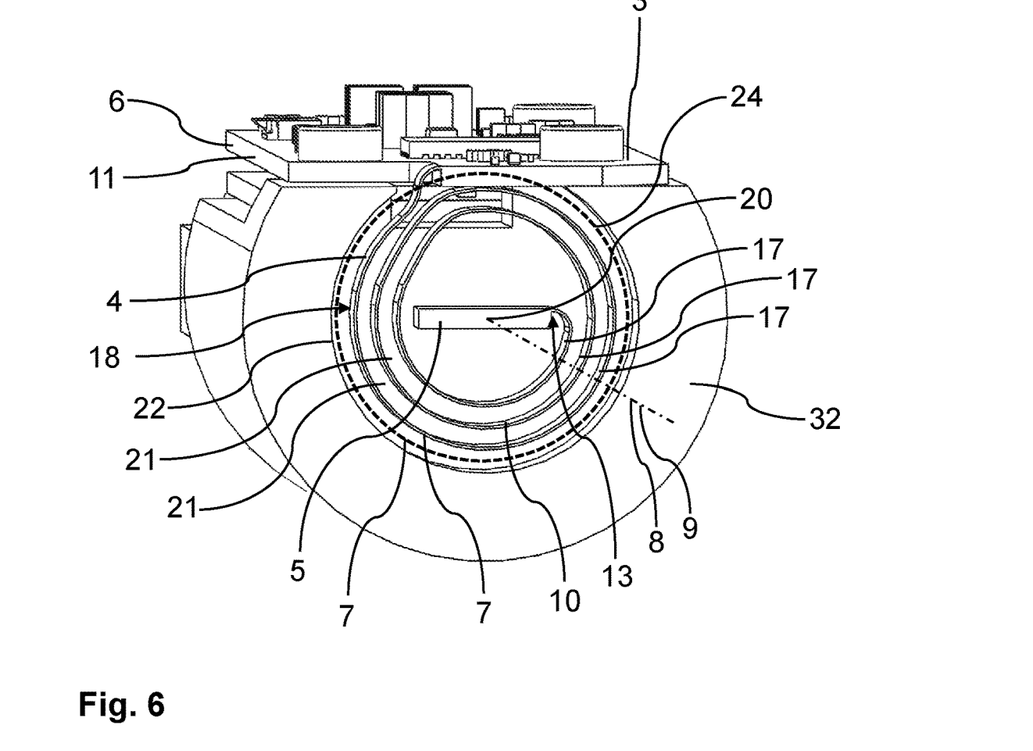
FIG. 6 shows a perspective frontal view of a cross section through the connecting element according to the invention in the region of the spiral spring.
Figure 7:
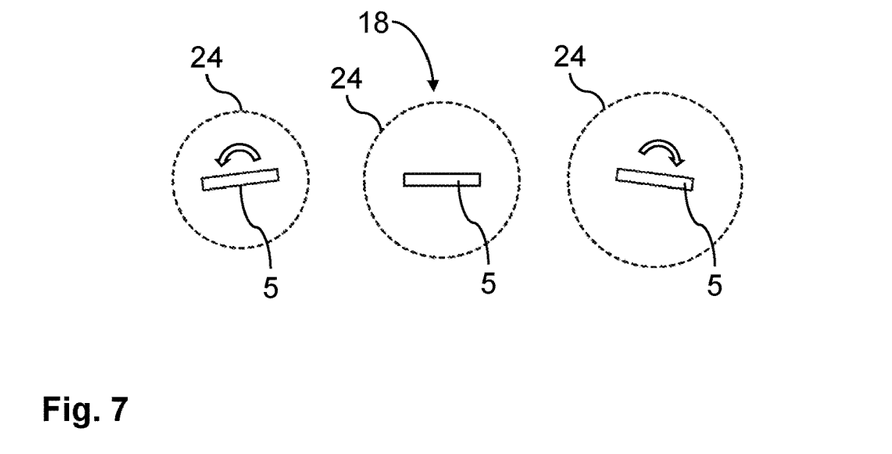
FIG. 7 shows a schematic illustration of the change of the outer circumference of the spiral spring from FIG. 6, depending on rotation of the connecting element.

As explained in FIGS. 6 and 7, the circumference 24 of the spiral spring 10 is changed as soon as the two functional units are rotated in relation to each other: in its inoperative position 18, illustrated in the central figure of FIG. 7, the spiral spring exerts only a very low resetting force, if any at all. If, by contrast, in the case of the exemplary embodiment shown in FIG. 6, the first rigid portion 5 is rotated toward the second rigid portion 6, as illustrated in the left figure in FIG. 7, the circumference 24 is reduced. In a corresponding manner, the circumference 24 of the spiral spring 10 is increased if the first rigid portion 5 is rotated as illustrated in the right figure of FIG. 7.

So that the spiral spring 10 can move in as resistance-free a manner as possible during the winding up and unwinding, a receiving space 22 (cf. FIG. 2) is provided in the endoscope 1, said receiving space receiving the winding 7 in a contact-free manner in the radial direction. By contrast, two stop surfaces 23 are formed in the axial direction on the heat sink 32, said stop surfaces axially limiting the movement of the spiral spring 10, during the rotation of the functional units 2a and 2b in relation to each other (cf. FIG. 2).

In the exemplary embodiment of a connecting element 3 according to the invention that is shown in FIG. 3, the transitions 12 between the central flexible portion 4 and the two rigid portions 5 and 6 of the printed circuit board 11 are arranged specifically in such a manner that the central portion 4 is oriented in the direction of the winding 7 and therefore runs transversely with respect to the axis of rotation 8. This permits the space-saving design of the flat spiral spring 10, as shown in FIG. 4.

It can furthermore be seen in FIG. 3 that the two rigid portions 5 and 6 each protrude over the central portion 4 in both directions by more than the width of the central portion 4. The protruding regions of the two rigid portions 5 and 6 therefore protrude out of the spiral spring 10, as shown in FIG. 4. This permits fastening of the connecting element 3 on both sides of the spiral spring 10 and therefore a self-supporting arrangement of the spiral spring 10. By contrast, it can readily be seen in FIGS. 4 and 2 that the regions of the rigid portions 5 and 6 which overlap with the winding 7 are arranged in a free-standing manner.

Figure 5:
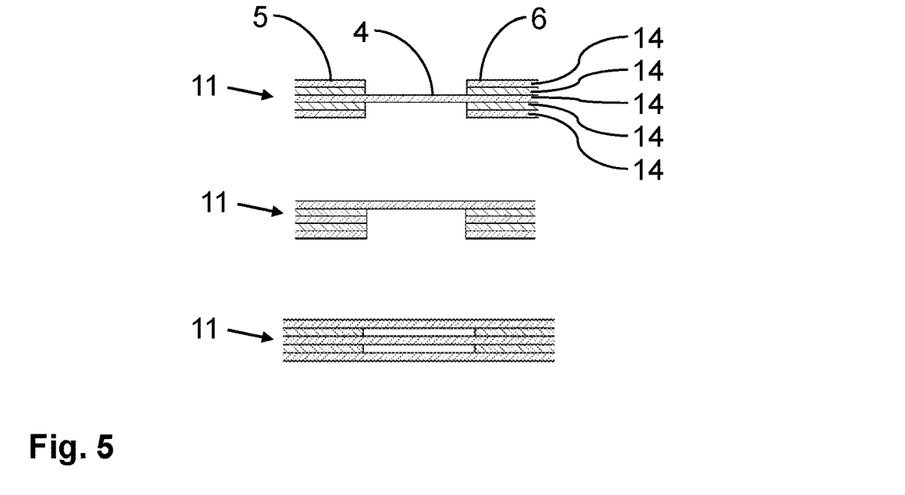
FIG. 5 shows cross-sectional views of various possibilities of refining the printed circuit board from FIGS. 3 and 4.

FIG. 5 shows a plurality of possible refinements of the printed circuit board 11 from FIGS. 3 and 4. The printed circuit board 11 is formed of a plurality of layers 14. In order to achieve the desired flexibility and elasticity of the central portion 4, individual layers of the layers 14 are completely omitted in this region. As the individual figures of FIG. 5 show, inner and outer layers 14 can be omitted here in the central portion 4. In all of the variants shown in FIG. 5, the number of layers in the central portion 4 is also reduced by at least 2, in comparison to the two rigid regions 5 and 6.

As indicated by the reference sign 13 in FIGS. 3, 4 and 6, a wedge 13 can in each case be formed at the transitions 12 between the central flexible portion 4 and the rigid portions 5, 6 in order to be able to better conduct away the bending forces occurring during the winding up and unwinding of the central portion 4. For the same reason, the first rigid portion 5 of the connecting element 3 is arranged in the center of the spiral spring 10 in the case of the exemplary embodiment shown in FIG. 6.

It can likewise be seen in FIG. 6 that the spiral spring 10 has the shape of an Archimedes spiral: the at least two turns 17 of the spiral are spaced apart equidistantly from one another in the inoperative position 18, which is illustrated in FIG. 6, wherein, as the angle of rotation increases, the radial position of a turn 17 increases linearly, and wherein the intermediate spaces 21 between the turns 17 are kept free. In other words, the central portion 4 is therefore specifically not wound up onto a winding body, but rather is arranged in a self-supporting manner. These refinements of the spiral spring are overall favorable in order to accommodate a plurality of turns in a narrow space and to permit as simple an installation as possible.

In summary, the invention permits a high-frequency transmission of data between functional units 2a, 2b, which are mounted rotatably with respect to each other, of an endoscope 1, wherein the functional units 2a, 2b can in particular be electrically insulated from each other. For this purpose, the invention proposes an electric connecting element 3 which is rolled up transversely with respect to the transmission direction in a central flexible portion 4 and is fastened at its respective end portions 33 to the functional units 2a, 2b. Upon rotation of the functional units 2a, 2b in relation to each other, an uninterrupted electric connection can therefore also be obtained with consistent quality of the signal transmission. By rolling up the central portion 4 to form a winding 7 which is preferably configured in a self-supporting manner, a long term stable rotary degree of freedom for the connecting element 3 is created in a very simple manner and permits complex mechanical adjustment functions in the endoscope 1.

LIST OF REFERENCE SIGNS 1 endoscope
2a first functional unit
2b second functional unit
3 connecting element
4 (central) portion (wound)
5 first rigid portion
6 second rigid portion
7 windings
8 axis of rotation
9 winding axis
10 spiral spring
11 printed circuit board
12 transition
13 wedge
14 layer (of 11)
15 housing
16 rotary wheel (outer coupling element)
17 turn
18 inoperative position
19 electric leadthrough
20 center of rotation
21 intermediate spaces
22 receiving space
23 axial stop surface
24 circumference (of 7, 10)
25 camera control unit
26 monitor
27 handle
28 camera cable
29 endoscope shaft
30 endoscope tip
31 plug-in contacts
32 heat sink
33 end portion
34 electronic circuit

The invention claimed is:

1. An endoscope (1) comprising:
two functional units (2a, 2b) which are rotatable in relation to each other about a common axis of rotation (8);
an electric connecting element (3) by which the two functional units (2a, 2b) are electrically connected or connectable to one another, the connecting element (3) includes a flexible portion (4) that is placed into a winding (7),
the connecting element (3) has a first rigid portion (5) and a second rigid portion (6), and the flexible portion (4) is a central flexible portion (4) that connects the first rigid portion (5) and the second rigid portion (6) to each other, and
at least one of the first rigid portion (5) or the second rigid portion (6) protrudes over the central flexible portion (4) in a direction of the axis of rotation (8), and the first rigid portion (5) and the second rigid portion (6) overlap only in a region of the central flexible portion (4).

2. The endoscope (1) as claimed in claim 1, wherein the flexible portion (4) is arranged in a self-supporting manner, and the axis of rotation (8) coincides with a central winding axis (9) of the winding (7).

3. The endoscope (1) as claimed in claim 1, wherein the winding (7) is at least one of: in the form of a band, dimensionally stable, or arranged in a spiral.

4. The endoscope (1) as claimed claim 1, wherein the flexible portion (4) is elastically deformable transversely with respect to the axis of rotation (8).

5. The endoscope (1) as claimed in claim 1, wherein the flexible portion generates a prestress upon the winding (7).

6. The endoscope (1) as claimed in claim 1, wherein the winding (7) is designed as a band-shaped, spiral spring (10).

7. The endoscope (1) as claimed in claim 6, wherein when the two functional units (2a, 2b) rotate in relation to each other, and the spiral spring (10) permits a reversible elastic deformation of the connecting element (3) out of a rotated position.

8. The endoscope (1) as claimed in claim 1, wherein the central flexible portion (4) in each case contacts the two rigid portions (5, 6) in a direction of the winding (7), transversely with respect to the axis of rotation (8).

9. The endoscope (1) as claimed in claim 1, wherein the connecting element (3) is formed integrally from a multi-layered printed circuit board (11), and the flexible portion (4) is formed by a material weakening or material omission, or wherein a wedge (13) is formed at at least one transition (12) between one of the rigid portions (5, 6) and the central flexible portion (4), said wedge conducting away bending forces which occur to the transition (12).

10. The endoscope (1) as claimed in claim 9, wherein a number of layers of the printed circuit board (11) in the central flexible portion (4) is at least two less than a number of layers in the two rigid portions (5, 6), and, in order to obtain a uniform electrical impedance of the connecting element (3), a metalized layer of the printed circuit board (11) that is used for shielding is formed in a region of the central flexible portion (4) as a perforated grid, or wherein the printed circuit board (11) has strip conductors which are pressed onto individual layers of the printed circuit board.

11. The endoscope (1) as claimed in claim 1, wherein the first rigid portion (5) is connected non-rotatably to a housing (15) of the endoscope (1), and the second rigid portion (6) is connected non-rotatably to an inner coupling element which is arranged in an interior of the housing (15), and the endoscope (1) further comprises an outer coupling element (16) with which torques care transmittable to the inner coupling element from outside.

12. The endoscope (1) as claimed in claim 1, wherein the winding (7) at least one of forms at least two complete turns (17), or is designed as an Archimedes' spiral.

13. The endoscope (1) as claimed in claim 1, wherein at least one of: the winding (7) is wound from a flat blank, or turns (17) of the winding (7) are spaced apart from one another in an inoperative position (18).

14. The endoscope (1) as claimed in claim 1, further comprising a hermetic housing (15), the electric connecting element (3) is electrically insulated from the housing (15) and is arranged in an interior of the hermetic housing (15), the connecting element (3) includes at least one rigid portion (5, 6) that is held by an electric leadthrough (19) formed on the housing (15), and the first functional unit (2a) bears an image sensor and the second functional unit (2b) bears an object-side lens assigned to the image sensor.

15. The endoscope (1) as claimed in one claim 14, wherein the connecting element (3) is held only in each case in a region of the two rigid portions (5, 6), and the central flexible portion (4) is formed in a self-supporting manner, and one of the first or the second rigid portions (5, 6) is arranged in a center of rotation of the winding (7).

16. The endoscope (1) as claimed in claim 6, wherein intermediate spaces (21) are kept free between individual turns of the winding (7), such that the winding (7) can be wound up and unwound automatically without assistance, by rotation of the two functional units (2a, 2b) in relation to each other, or such that the winding (7) is held freely movable in a radial direction over an entire rotary adjustment range of the spiral spring (10).

17. The endoscope (1) as claimed in claim 1, wherein the winding (7) is arranged without a carrier and is kept in a spiral shape in a radial direction free from contact with other bodies based only on a dimensional stability of the winding, and the endoscope further includes a receiving space (22) that receives the winding (7) in a contact-free manner in the radial direction both during winding up and unwinding.

18. The endoscope (1) as claimed in claim 1, wherein at least one of the first or the second functional unit (2b) provides at least one axial stop surface (23) which axially limits a movement of the winding (7), during the rotation of the functional units (2a, 2b) in relation to each other, and the connecting element (3) bears an electronic circuit (34) in at least one end portion (33) thereof.

* * * * *